United States Patent [19]

Siegmund

[11] 4,290,421
[45] Sep. 22, 1981

[54] FIBERSCOPE

[75] Inventor: Walter P. Siegmund, Woodstock, Conn.

[73] Assignee: American Optical Corporation, Southbridge, Mass.

[21] Appl. No.: 161,725

[22] Filed: Jun. 23, 1980

Related U.S. Application Data

[63] Continuation of Ser. No. 1,670, Jan. 8, 1979, abandoned.

[51] Int. Cl.³ .............................................. A61B 1/06
[52] U.S. Cl. ...................................... 128/6; 138/120
[58] Field of Search ...................................... 128/3-6, 128/8, 303.15; 351/241; 350/96.26; 138/120, 108, 115-117

[56] References Cited

U.S. PATENT DOCUMENTS

| | | | |
|---|---|---|---|
| 3,091,235 | 5/1963 | Richards | 128/6 |
| 3,253,524 | 5/1966 | Ashizawa et al. | 128/6 UX |
| 3,266,059 | 8/1966 | Stelle | 128/42 R |
| 3,572,325 | 3/1971 | Bazell et al. | 128/6 |
| 3,913,568 | 10/1975 | Carpenter | 128/11 |
| 3,929,164 | 12/1975 | Richter | 138/120 |

Primary Examiner—Stephen C. Pellegrino
Attorney, Agent, or Firm—Alan H. Spencer

[57] ABSTRACT

Universal articulation of the end of a medical or industrial fiberscope is accomplished with three-wire control for reducing space requirements in small diameter instruments.

5 Claims, 4 Drawing Figures

FIBERSCOPE

This is a continuation of application Ser. No. 1,670, filed Jan. 8, 1979 now abandoned.

BACKGROUND OF THE INVENTION

1. Field of the Invention:

Fiberoptic endoscope with particular reference to improvements in means for effecting remote articulation of ends of small diameter medical and industrial fiberscopes.

2. Discussion of the Prior Art:

Remote articulation of the distal ends of medical and industrial fiberscopes is commonly provided. This is either articulation in one plane only (two-way) or articulation in all planes (four-way). Two-way devices require two wires leading from the fiberscope tip to its proximal end and prior art four-way devices require four wires, two for each of two mutually perpendicular planes. The structures of U.S. Pat. Nos. 3,913,568 and 3,091,235 are respectively exemplary of two-way and four-way devices.

In small diameter fiberscopes, e.g. bronchoscopes of 5 to 6 mm in overall diameter, the heretofore trade-off of image-conducting and object-illuminating fiber space for manipulating wires, or vice versa, has posed the problem of selection between larger or more intense image conductance and four-way, two-way or no remotely-controlled distal articulation of the fiberscope. For example, the advantage of four-way articulation has required the sacrifice of a number of light-conducting fibers and/or biopsy channeling whose total cross-sectional area corresponds to that of four control wires and their guides.

Accordingly, in the interest of increasing image size and/or illuminating bundle size in universally articulable fiberscopes of restricted overall diametral sizes, it is an object of this invention to accomplish remotely-controlled distal articulation in all planes (4-way) with less than four control wires.

More particularly, it is an object of the invention to accomplish four-way distal articulation of a fiberscope with a three-wire system which affords greater than usual space for fiberscope light-conducting fibers and/or channeling.

Another object is to provide improved distal vertebration in an articulable fiberscope.

Still another object is to overcome the heretofore complexity of fiberscope remote control apparatuses by structural simplification and reduction of component parts.

Other objects and advantages of the invention will become apparent from the following description.

SUMMARY OF THE INVENTION

The foregoing objects and their corollaries are accomplished with three-wire control which provides for fiberscope articulation in all planes (4-way) with space available for light-conducting fibers of biopsy channeling and like in place of the usual fourth wire and wire guide.

Centrally hinged hollow vertebrae, constrained against lateral displacement, comprise the supporting structure for distal articulation with light-conducting fibers and biopsy channeling or the like extended therethrough around the hinging. Three operating wires guided through peripheral portions of the vertebrae at approximately equally circumferentially spaced locations afford control means for articulation of the fiberscope. These simple centrally hinged fiberscope vertebrae avoid the costliness and complexity of previously pinned, socketed or similarly jointed fiberscope vertebrae.

Details of the invention will become more readily apparent from the following description when taken in conjunction with the accompanying drawings.

IN THE DRAWINGS

DESCRIPTION OF THE PREFERRED EMBODIMENTS

Figure 1:
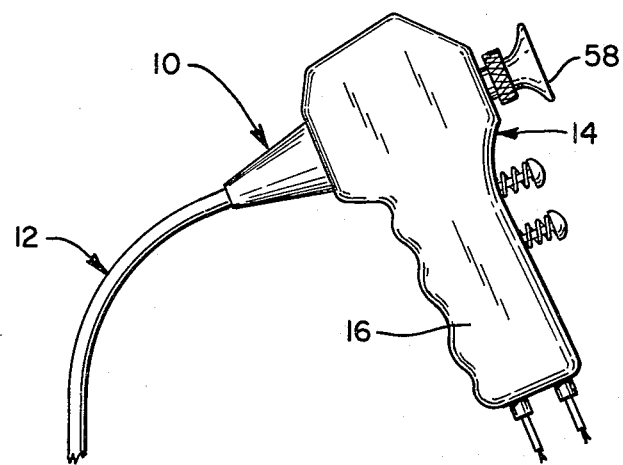
FIG. 1 is an illustration of a distally vertebrated remotely articulable fiberscope incorporating an embodiment of the present invention.

Fiberscope 10 of FIG. 1 having probe 12 and head 14 with operating handle 16 is distally universally articulable as illustrated with broken lines 18, i.e. with remote operation at head 14 the distal portion 20 of probe 12 may be flexed in all directions away from the position of full line illustration. This articulation is known in the art as "four-way" since it has heretofore required the use of four operating wires, two for each of two mutually perpendicular planes. With improved vertebration, however, the present invention affords full four-way articulation with three-wire control as follows:

Distal vertebration in portion 20 of probe 12 comprises a series of centrally hinged vertebrae 22 secured against longitudinal and lateral misalignment with wire 24.

Vertebrae 22 are each internally webbed to provide three approximately equally circumferentially spaced channels 26, 27 and 28 through which illuminating and image-conducting fiber bundles 32 and 34 (FIG. 2) and/or biopsy channeling (not shown) may be extended.

In each case of each vertebra, webs 36, 38 and 40 (FIGS. 3 and 4) support double-ended hinge portion 42 through which retaining wire 24 is extended.

Vertebrae 22 are fixed against relative longitudinal displacement by anchoring of opposite ends of wire 24, one in fiberscope tip 44 and the other in retainer 46. Abutting end faces 48 of hinge portions 42 allow universal hinging of vertebrae 22. Hinging is effected by pulling forces applied to the marginal portion of fiberscope tip 44, i.e. by one or more of operating wires 50, 52, 54.

Wires 50, 52, 54 extending from fiberscope head 14 are loosely threaded through retainer 46 and marginal portions of vertebrae 22 and are anchored in tip 44 at approximately 120° circumferential intervals. The anchoring of wires 50, 52, 54 and retaining wire 24 in fiberscope tip 44 may be accomplished by soldering, brazing, swaging or combinations thereof, i.e. by any fastening scheme deemed appropriate to the artisan.

Remote ends of the three operating wires 50, 52, 54 may be manipulated as follows to effect articulation of distal portion 20 of probe 14;

All three wires may be manipulated independently by lever operation or electrically, hydraulically or pneumatically with servo drive. Alternatively, two wires may be activated as suggested above with the third wire spring loaded to return distal portion 20 to its unflexed position. The latter is a presently preferred version of manipulation since it minimizes the degree of operating technique and learning process required of an operator.

Lever operated actuating means applicable to the threewire system of the present invention is illustrated in U.S. Pat. No. 3,091.235.

Figure 2:
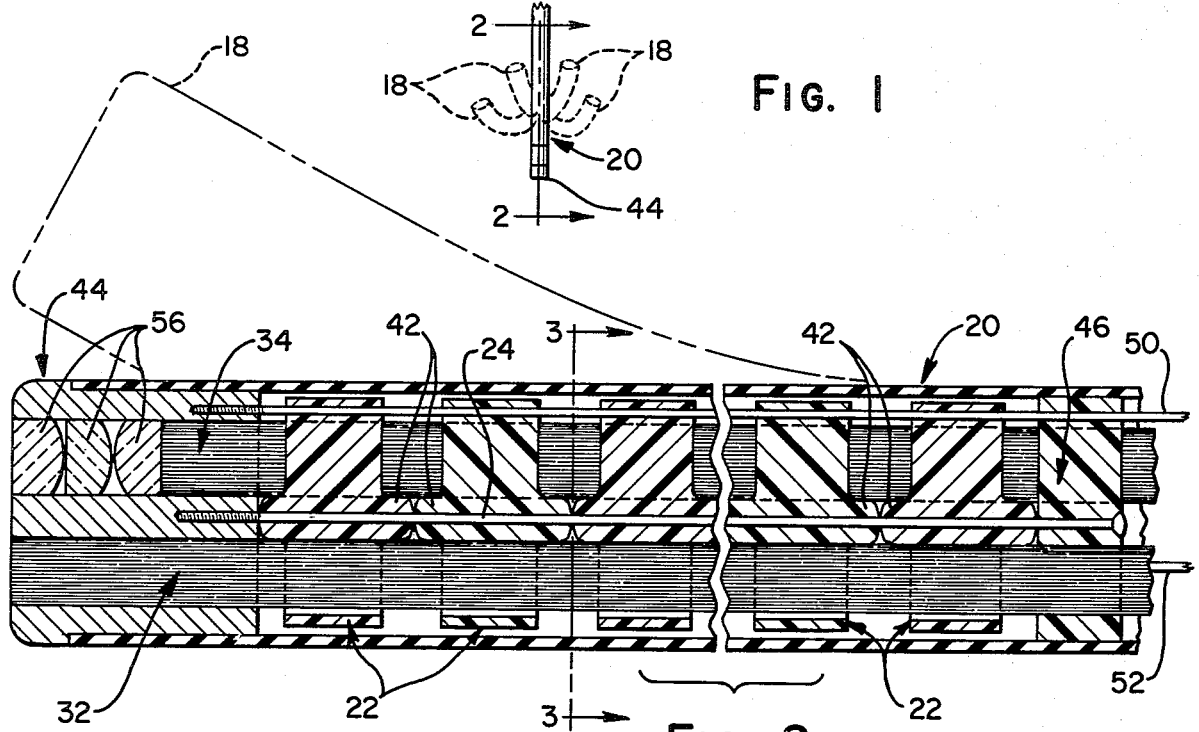
FIG. 2 is a greatly enlarged cross-sectional view taken approximately along line 2—2 of FIG. 1.
Figure 3:
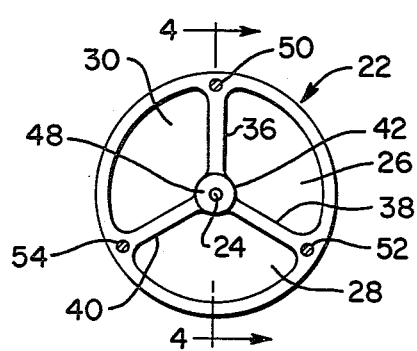
FIG. 3 is a face view of a vertebra of the structure illustrated in FIG. 2 taken along line 3—3 with adjoining and surrounding components of the fiberscope omitted for clarity of illustration.
Figure 4:
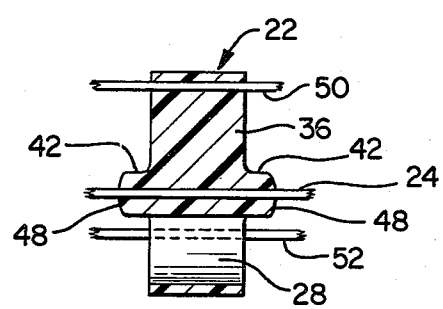
FIG. 4 is a cross-sectional view taken along line 4—4 of FIG. 3.

For reasons of clarity of illustration of vertebrae 22, fiberoptic light-conducting bundles and/or biopsy channeling or other tubing have not been shown in FIGS. 3 and 4. It should be understood, however, that the entire cross-sectional area of each of channels 26, 28 and 30 is available for reception of such light-conducting means and/or channeling. As shown in FIG. 2, for example, light-conducting bundle 32 is extended through one of channels 26, 28 and 30 of the succession of vertebrae 22 and thence through fiberscope tip 44. By such means, objects to be examined with the fiberscope may be illuminated with light from a remote source located in head 14, for example.

Bundle 34 of optical fibers extended through another of channels 26, 28 and 30 of vertebrae 22 is terminated in tip 44 with objective lenses 56 adapted to form images of an object illuminated by bundle 32. In the usual fashion, such images may be transmitted by internal reflection through bundle 34 to a viewing plane in fiberscope head 14 and viewed directly or with the aid of an eyepiece 58.

Remaining space through vertebrae 22, e.g. a third of channels 26, 28 and 30, may be occupied by biopsy channeling or other tubing and/or additional optical fibers. The use of channeling in a fiberscope can be seen in drawings of the structure of U.S. Pat. No. 3,091,235.

Those skilled in the art will readily appreciate that there are various modifications and adaptations of the precise form of the invention here shown which may suit particular requirements and that the foregoing illustrations are not to be interpreted as restrictive of the invention beyond that necessitated by the following claims.

I claim:

1. In a fiberscope probe for use in an endoscope having an articulable distal section, the improvement comprising:

a series of webbed vertebrae in said distal section of said probe each having three approximately equally circumferentially spaced openings through which endoscope illuminating and image-conducting fiber bundles and biopsy channelling may be extended and a centrally disposed doubled-ended hinge portion, said hinge portions being adjoined successionally;

means for retaining said hinge portions in said adjoined relationship while permitting universal hinging thereof one relative to another; and operating wire means extending peripherally through said series of vertebrae for use in effecting said hinging thereof, said operating wire means comprising three wires approximatey equally circumferentially spaced from one another about said periphery of said vertebrae, said wires being anchored in said fiberscope probe adjacent one end of said series of vertebrae.

2. The improvement according to claim 1 wherein said retaining means comprises a wire extending substantially centrally through said succession of hinge portions, said wire being anchored against longitudinal displacement adjacent each of opposite ends of said series of vertebrae.

3. The improvement according to claim 1 wherein said hinge portions are supported by webs extending radially from peripheral portions of said vertebrae.

4. The improvement according to claim 1 wherein said fiberscope is provided with a rigid tip at said one end of said series of vertebrae into which said three operating wires are anchored.

5. The improvement according to claim 4 wherein said fiberscope probe further includes rigid anchoring means for one end of said centrally extending wire, said anchoring means being adjacent an end of said series of vertebrae oppositely of said fiberscope tip and the opposite end of said centrally extending wire being anchored in said fiberscope tip.

* * * * *